United States Patent
Gebert-Schwarzwaelder et al.

(10) Patent No.: US 10,561,594 B2
(45) Date of Patent: Feb. 18, 2020

(54) AGENT FOR STABILIZING KERATIN FIBERS WITH 5-RING HETEROCYCLES

(71) Applicant: Henkel AG & Co. KGaA, Duesseldorf (DE)

(72) Inventors: Antje Gebert-Schwarzwaelder, Neuss (DE); Ralph Nemitz, Juechen (DE); Astrid Kroos, Monheim (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 15/786,720

(22) Filed: Oct. 18, 2017

(65) Prior Publication Data
US 2018/0140525 A1    May 24, 2018

(30) Foreign Application Priority Data
Nov. 24, 2016 (DE) .............. 10 2016 223 327.0

(51) Int. Cl.
| | | |
|---|---|---|
| *A61K 8/22* | (2006.01) | |
| *A61K 8/23* | (2006.01) | |
| *A61K 8/49* | (2006.01) | |
| *A61Q 5/00* | (2006.01) | |

(52) U.S. Cl.
CPC ............. *A61K 8/4973* (2013.01); *A61K 8/22* (2013.01); *A61K 8/23* (2013.01); *A61Q 5/00* (2013.01)

(58) Field of Classification Search
CPC .......... A61K 8/22; A61K 8/23; A61K 8/4973; A61Q 5/00; A61Q 5/04; A61Q 5/08
See application file for complete search history.

(56) References Cited

FOREIGN PATENT DOCUMENTS

| | | |
|---|---|---|
| DE | 19617395 A1 | 1/1997 |
| DE | 202017101867 U1 | 7/2017 |
| DE | 202017101868 U1 | 7/2017 |
| EP | 2478892 A1 | 7/2012 |
| JP | 2007176826 A | 7/2007 |
| WO | 2005074875 A2 | 8/2005 |

OTHER PUBLICATIONS

Intellectual Property Office, Search Report under Section 17(5) for United Kingdom Patent Application No. GB1717146.3 dated Jul. 2, 2018.
Kazancioglu, Akin et al., "Photooxygenation of Azidoalkyl Furans: Catalyst-Free Triazole and New Endoperoxide Rearrangement", Organic Letters, vol. 15, No. 18, pp. 4790-4793, 2013.
Memarian, Hamid R. et al., "Synthesis of Some New Unsymmetrically Substituted 1,4-Dihydropyridines", Zeitschrift Naturforschung 61b, pp. 50-56, 2006.

*Primary Examiner* — Zohreh A Fay
(74) *Attorney, Agent, or Firm* — Lorenz & Kopf, LLP

(57) ABSTRACT

The subject matter of the present disclosure are agents for stabilizing keratin fibers, more particularly human hair, containing in a cosmetic carrier:
(a) at least one compound of the formula (I)

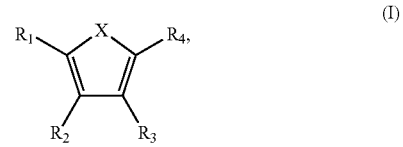

wherein
X denotes oxygen (—O—), sulfur (—S—) or a grouping —$NR_5$—.

5 Claims, No Drawings

AGENT FOR STABILIZING KERATIN FIBERS WITH 5-RING HETEROCYCLES

CROSS-REFERENCE TO RELATED APPLICATION

This application claims priority to German Patent Application No. 10 2016 223 327.0, filed Nov. 24, 2016, which is incorporated herein by reference in its entirety.

TECHNICAL FIELD

The present disclosure relates to the cosmetic sector. The subject matter of the present disclosure relates to agents for stabilizing keratin fibers, more particularly human hair, which contain, in a cosmetic carrier, at least one heterocyclic compound of the formula (I).

BACKGROUND

Human hair is exposed to highly-diverse environmental influences over a prolonged period—in the case of long hair, even over several years. These environmental influences can damage and destabilize the hair fibers. Cosmetic treatments such as permanent waves, oxidative coloring and event treatments during which the hair is exposed to elevated temperatures (e.g. the use of hair straighteners) can also severely damage the hair. All these influences and treatments cause destructive changes to the hair structure, and these can culminate in impaired combability of dry and wet hair, less shine and reduced softness.

There is therefore a need to further improve hair treatment products and find active ingredients which stabilize the structure of the keratin fibers.

In the prior art, keratin cross-linkers are often used to achieve structural stabilization of the hair structure. Keratin cross-linkers are unsaturated, monomeric compounds with a molecular mass of less than about 500 g/mol. When keratin cross-linkers are applied to hair, they are able to diffuse well into the hair fiber due to their small molecular mass. Inside the hair fiber, the keratin cross-linkers then form—either with the hair fiber itself or with other cross-linker molecules—adducts, said adduct formation occurring at the double bond of each cross-linker molecule.

Corresponding keratin cross-linkers are described, for example, in EP 2478892 A1. In chemical terms, this cross-linking is effectively the addition to a double bond. In order to activate the double bond of the keratin cross-linker, this is often located in close proximity of a group with strong electron-withdrawing properties (a carboxyl group, for example). The addition reaction can also be further facilitated by the use of initiators. In EP 2478892 A1, persulfates, peracids or azo compounds, for example, can also be used. In this context, an acid range of from about 4.0 to about 6.9 is described as the optimum pH value for this reaction.

In the studies on which this application is based, however, it has now been found that the keratin cross-linkers described in EP 2478892 A1 are not optimally adapted to the bleaching of keratin fibers.

The present disclosure therefore addresses the problem of providing an agent to stabilize keratin fibers, more particularly human hair. The active substances used in this agent should have a stabilizing effect particularly on the inner structure of the keratin fibers. Moreover, the active substances used in the agent ought to be compatible with a large number of cosmetic treatment procedures (such as bleaching agents, permanent wave agents, etc.).

BRIEF SUMMARY

Disclosed is an agent for stabilizing keratin fibers comprising a cosmetic carrier and (a) at least one compound of formula (I):

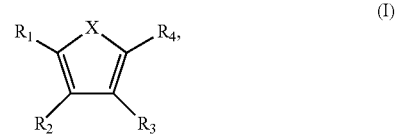

wherein:
X denotes oxygen (—O—), sulfur (—S—) or a grouping —NR$_5$—,
R$_1$, R$_2$, R$_3$, R$_4$ denote independently a hydrogen atom, a C$_1$-C$_6$-alkyl group, a C$_2$-C$_6$-alkenyl group, a hydroxy-C$_1$-C$_6$-alkyl group, a C$_2$-C$_6$-alkanoyl group, a carboxyl group, a C$_1$-C$_6$-alkoxy-carbonyl group, a halogen atom, an aryl group, an aryl-C$_1$-C$_6$-alkyl group or the grouping Y,
R$_5$ denotes a C$_1$-C$_6$-alkyl group, a C$_2$-C$_6$-alkenyl group or an aryl group,
Y denotes a grouping of the formula (II):

and
R$_6$, R$_7$ denote independently a hydrogen atom, a C$_1$-C$_6$-alkyl group, a C$_2$-C$_6$-alkenyl group, a halogen atom, a hydroxy-C$_1$-C$_6$-alkyl group, a C$_2$-C$_6$-alkanoyl group, a carboxyl group, a C$_1$-C$_6$-alkoxy-carbonyl group, a carbamoyl group, a C$_1$-C$_6$-alkylaminocarbonyl group or a di(C$_1$-C$_6$)alkylaminocarbonyl group.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It has now unexpectedly emerged that the aforementioned problem can be solved to the fullest extent by using a hair treatment agent containing at least one of the compounds in the formula (I) to stabilize the keratin fibers.

A first subject matter of the present disclosure is an agent for stabilizing keratin fibers, more particularly human hair, containing in a cosmetic carrier.

(a) at least one compound of the formula (I)

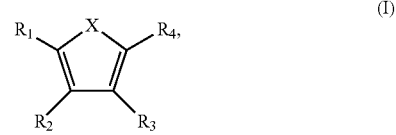

wherein

X denotes oxygen (—O—), sulfur (—S—) or a grouping —NR$_5$—,

R$_1$, R$_2$, R$_3$, R$_4$ denote independently a hydrogen atom, a C$_1$-C$_6$-alkyl group, a C$_2$-C$_6$-alkenyl group, a hydroxy-C$_1$-C$_6$-alkyl group, a C$_2$-C$_6$-alkanoyl group, a carboxyl group, a C$_1$-C$_6$-alkoxy-carbonyl group, a halogen atom, an aryl group, an aryl-C$_1$-C$_6$-alkyl group or the grouping Y, R$_5$ denotes a C$_1$-C$_6$-alkyl group, a C$_2$-C$_6$-alkenyl group or an aryl group, Y denotes a grouping of the formula (II),

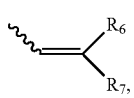

(II)

R$_6$, R$_7$ denote independently a hydrogen atom, a C$_1$-C$_6$-alkyl group, a C$_2$-C$_6$-alkenyl group, a halogen atom, a hydroxy-C$_1$-C$_6$-alkyl group, a C$_2$-C$_6$-alkanoyl group, a carboxyl group, a C$_1$-C$_6$-alkoxy-carbonyl group, a carbamoyl group, a C$_1$-C$_6$-alkylaminocarbonyl group or a di(C$_1$-C$_6$)alkylaminocarbonyl group.

It emerged that, after applying the agent as contemplated herein, less hair breakage occurred during the subsequent combing step and the stability of the fibers was higher. The increased fiber stability can be established by employing DSC (Difference Scanning Calorimetry) measurements, for example. Moreover, the hair lost less elasticity than after the application of bleaching agents that are not in accordance with the present disclosure. The elasticity of a fiber of hair was able to be established through stress-strain measurements, for example.

The agents as contemplated herein contain the elements useful to the present disclosure in a cosmetic carrier. Such carriers include creams, emulsions, gels or surfactant-containing, foaming solutions such as shampoos, foaming aerosols, foam formulations or other preparations suitable for application on the hair.

In this present disclosure, anhydrous-alcoholic solutions are, more particularly, anhydrous solutions containing from about 0.1 to about 70 percentage by weight of a C$_1$-C$_4$ alcohol, more particularly ethanol and/or isopropanol. The agents as contemplated herein can also contain other organic solvents, such as methoxybutanol, benzyl alcohol, ethyldiglycol or 1,2-propylene glycol. All water-soluble organic solvents are acceptable.

(a) Compounds of the Formula (I)

As the component (a), the agent as contemplated herein for stabilizing the keratin fibers contains (a) at least one compound of the formula (I)

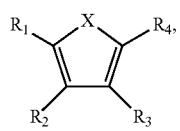

(I)

wherein

X denotes oxygen (—O—), sulfur (—S—) or a grouping —NR$_5$—,

R$_1$, R$_2$, R$_3$, R$_4$ denote independently a hydrogen atom, a C$_1$-C$_6$-alkyl group, a C$_2$-C$_6$-alkenyl group, a hydroxy-C$_1$-C$_6$-alkyl group, a C$_2$-C$_6$-alkanoyl group, a carboxyl group, a C$_1$-C$_6$-alkoxy-carbonyl group, a halogen atom, an aryl group, an aryl-C$_1$-C$_6$-alkyl group or the grouping Y, R$_5$ denotes a C$_1$-C$_6$-alkyl group, a C$_2$-C$_6$-alkenyl group or an aryl group, Y denotes a grouping of the formula (II),

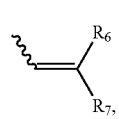

(II)

R$_6$, R$_7$ denote independently a hydrogen atom, a C$_1$-C$_6$-alkyl group, a C$_2$-C$_6$-alkenyl group, a halogen atom, a hydroxy-C$_1$-C$_6$-alkyl group, a C$_2$-C$_6$-alkanoyl group, a carboxyl group, a C$_1$-C$_6$-alkoxy-carbonyl group, a carbamoyl group, a C$_1$-C$_6$-alkylaminocarbonyl group or a di(C$_1$-C$_6$)alkylaminocarbonyl group.

The radical X is a grouping in the unsaturated, heterocyclic 5-ring system. X can denote either oxygen (—O—), sulfur (—S—) or a grouping —NR$_5$—.

If X denotes an oxygen atom (—O—), the compounds of the formula (I) as contemplated herein are derivatives of furan. If X denotes a sulfur (—S—), the compounds of the formula (I) as contemplated herein are derivatives of thiophene. If X denotes a grouping —NR$_5$—, the compounds of the formula (I) as contemplated herein are derivatives of pyrol.

As shown in DSC measurements, the nature of radical X influences the stabilizing abilities of the compounds of the formula (I). Good effects can be achieved when radical X denotes an oxygen atom (—O—).

In one embodiment, an agent for stabilizing keratin fibers as contemplated herein contains at least one compound of the formula (I), in which radical X denotes oxygen (—O—).

Radicals R$_1$, R$_2$, R$_3$, R$_4$ denote independently a hydrogen atom, a C$_1$-C$_6$-alkyl group, a C$_2$-C$_6$-alkenyl group, a hydroxy-C$_1$-C$_6$-alkyl group, a C$_2$-C$_6$-alkanoyl group, a carboxyl group, C$_1$-C$_6$-alkoxy-carbonyl group, a halogen atom, an aryl group, an aryl-C$_1$-C$_6$-alkyl group or the grouping Y.

Radical R$_5$ denotes a hydrogen atom, a C$_1$-C$_6$-alkyl group, a C$_2$-C$_6$-alkenyl group or an aryl group.

The grouping Y constitutes a grouping of the formula (II),

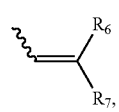

(II)

wherein radicals R$_6$, R$_7$ denote in turn a hydrogen atom, a C$_1$-C$_6$-alkyl group, a C$_2$-C$_6$-alkenyl group, a halogen atom, a hydroxy-C$_1$-C$_6$-alkyl group, a C$_2$-C$_6$-alkanoyl group, a carboxyl group, C$_1$-C$_6$-alkoxy-carbonyl group, a carbamoyl group, a C$_1$-C$_6$-alkylaminocarbonyl group or a di(C$_1$-C$_6$) alkylaminocarbonyl group.

Examples of the substituents R$_1$, R$_2$, R$_3$, R$_4$, R$_5$, R$_6$ and R$_7$ stated in formula (I) are shown below:

Examples of C$_1$-C$_6$-alkyl groups are —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, —C(CH$_3$)$_3$, —(CH$_2$)$_4$CH$_3$, —(CH$_2$)$_5$CH$_3$. In one embodiment, the alkyl radicals are methyl and ethyl.

Examples of $C_2$-$C_6$-alkenyl groups are vinyl, prop-2-enyl (allyl), 2-methyl-prop-2-enyl, but-3-enyl, but-2-enyl, pent-4-enyl or pent-3-enyl.

Examples of $C_2$-$C_6$-hydroxyalkyl groups are —$CH_2$—$CH_2$—OH, —$CH_2$—$CH_2$—$CH_2$—OH, —$CH_2$—CH(OH)—$CH_3$, —$CH_2$—$CH_2$—$CH_2$—$CH_2$—OH, the —$CH_2$—$CH_2$—OH group being employed in an embodiment.

The ethanoyl group (—C(O)—$CH_3$), which is alternatively referred to as an acetyl group, can be stated as an example of a $C_2$-$C_6$-alkanoyl group. Other suitable $C_2$-$C_6$-alkanoyl groups are the n-propanoyl group (—C(O)—$CH_2$—$CH_3$) or the n-butanoyl group (—(C(O)—$CH_2$—$CH_2$—$CH_3$). The ethanoyl group (and/or acetyl group) is employed in an embodiment.

The carboxyl group is the group —COOH. The hydrogen atom of the carboxyl group is acidic, and therefore the (protonated) carboxyl group—more particularly in a hydrous cosmetic carrier—can also be in equilibrium with its deprotonated form.

Examples of $C_1$-$C_6$-alkoxy-carbonyl groups are the methoxycarbonyl group (—C(O)$OCH_3$) or the ethoxycarbonyl group (—C(O)$OCH_2CH_3$). An example of an aryl group is a phenyl group.

A halogen atom as contemplated herein is a chlorine atom, a bromine atom and a fluorine atom. Chlorine and bromine are employed in an embodiment.

In an embodiment, examples for an aryl-$C_1$-$C_6$-alkyl group are the benzyl group (i.e. the phenylmethyl group) and the 2-phenylethyl group.

A carbamoyl group as contemplated herein is the group —C(O)$NH_2$.

Examples of a $C_1$-$C_6$-alkylaminocarbonyl group are the groups —C(O)NH($CH_3$), —C(O)NH($CH_2CH_3$) and —C(O)NH($CH_2CH_2CH_3$).

Examples of a di($C_1$-$C_6$)alkylaminocarbonyl group are the groups —C(O)N($CH_3$)$_2$ and C(O)N($CH_2CH_3$).

It emerged that the compounds of formula (I), where at least one of the radicals from $R_1$, $R_2$, $R_3$ and $R_4$ denote a carboxyl group (—COOH), a $C_1$-$C_6$-alkoxycarbonyl group or the grouping Y, achieved good fiber protection.

In a further embodiment, an agent for stabilizing keratin fibers as contemplated herein contains at least one compound of the formula (I), where at least one of the radicals from $R_1$, $R_2$, $R_3$ and $R_4$ denote a carboxyl group (—COOH), a $C_1$-$C_6$-alkoxycarbonyl group or the grouping Y.

It also emerged that the compounds of the formula (I) are suitable for solving the problem addressed by the present disclosure if $R_1$, $R_2$, $R_3$ denote independently a hydrogen atom or a $C_1$-$C_6$-alkyl group, and $R_4$ denotes a carboxyl group (—COOH), a $C_1$-$C_6$-alkoxy-carbonyl group or the grouping Y.

In an embodiment, an agent for the stabilizing of keratin fibers as contemplated herein (a) contains at least one compound of the formula (I), wherein $R_1$, $R_2$, $R_3$ denote independently a hydrogen atom or a $C_1$-$C_6$-alkyl group, and $R_4$ denotes a carboxyl group (—COOH), a $C_1$-$C_6$-alkoxy-carbonyl group or the grouping Y.

Moreover, the compounds of the formula (I), where at least one of the radicals $R_1$, $R_2$, $R_3$ and $R_4$ denote the grouping Y, wherein Y denotes in turn the grouping of the formula (II), have proved to be suitable.

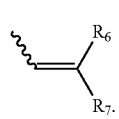

(II)

In the structural formula (II), the wavy line represents the bond between the double bond and the heterocyclic 5-ring. If, for example, radical $R_4$ denotes grouping Y, the following structure (III) applies

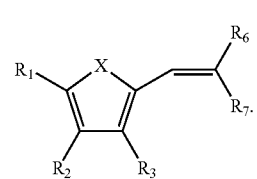

(III)

In a further embodiment, an agent for stabilizing keratin fibers, more particularly human hair, containing the following in a cosmetic carrier, is as follows:

(a) at least one compound of the formula (IIIa)

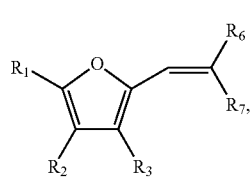

(IIIa)

wherein $R_1$, $R_2$, $R_3$, denote independently a hydrogen atom, a $C_1$-$C_6$-alkyl group, a $C_2$-$C_6$-alkenyl group, a hydroxy-$C_1$-$C_6$-alkyl group, a $C_2$-$C_6$-alkanoyl group, a carboxyl group, $C_1$-$C_6$-alkoxy-carbonyl group, a halogen atom, an aryl group, an aryl-$C_1$-$C_6$-alkyl group or the grouping Y, and $R_6$, $R_7$ denote independently a hydrogen atom, a $C_1$-$C_6$-alkyl group, a $C_2$-$C_6$-alkenyl group, a halogen atom, a hydroxy-$C_1$-$C_6$-alkyl group, a $C_2$-$C_6$-alkanoyl group, a carboxyl group, $C_1$-$C_6$-alkoxy-carbonyl group, a carbamoyl group, a $C_1$-$C_6$-alkylaminocarbonyl group or a di($C_1$-$C_6$)alkylaminocarbonyl group.

As already described above, a stabilization of the keratin fiber was observed when a compound of the formula (I), wherein at least one or the radicals $R_1$, $R_2$, $R_3$ and $R_4$ denotes the grouping Y, was used. In this context, an advantageous effect has been proven to occur when radicals $R_6$ and $R_7$ denote independently a $C_2$-$C_6$-alkanoyl group, a carboxyl group or a $C_1$-$C_6$-alkoxy-carbonyl group.

In an embodiment, an agent for the stabilizing of keratin fibers as contemplated herein (a) contains at least one compound of the formula (I), wherein at least one of the radicals $R_1$, $R_2$, $R_3$ and $R_4$ denotes the grouping Y and $R_6$, $R_7$ denote independently a $C_2$-$C_6$-alkanoyl group, a carboxyl group or a $C_1$-$C_6$-alkoxy-carbonyl group.

In a further embodiment, an agent for stabilizing keratin fibers, more particularly human hair, containing the following in a cosmetic carrier, is as follows:

(a) at least one compound of the formula (I)

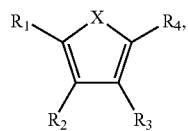

(I)

wherein

X denotes oxygen (—O—)

$R_1$ denotes a hydrogen atom or a $C_1$-$C_6$-alkyl group, $R_2$ and $R_3$ both denote a hydrogen atom, $R_4$ denotes a carboxyl group, $C_1$-$C_6$-alkoxy-carbonyl group or for the grouping Y, Y denotes a grouping of the formula (II),

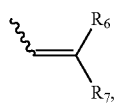

(II)

and $R_6$, $R_7$ denote independently a $C_2$-$C_6$-alkanoyl group, a carboxyl group or a $C_1$-$C_6$-alkoxy-carbonyl group.

Agents for stabilizing keratin fibers as contemplated herein are exemplified in that they contain at least one compound of the formula (I), which is selected from 2-vinylfuran

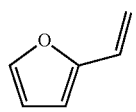

2-[(E/Z)-1-propenyl]furan

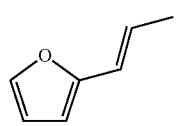

2-(2-methyl-1-propenyl)furan

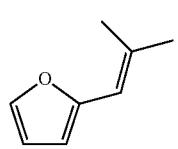

3-(2-furylmethylene)pentane-2,4-dione

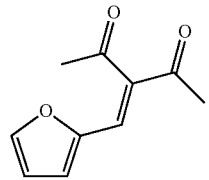

2-(2-furylmethylene)propanediol acid

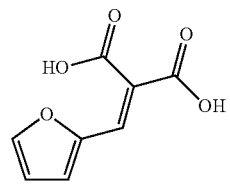 [SMILES: O=C(O)C(=Cc1ccco1)C(=O)O]

dimethyl 2-(2-furylmethylene)propanedioate

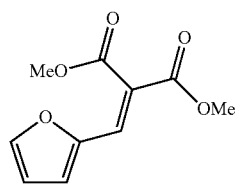 [SMILES: COC(=O)C(=Cc1ccco1)C(=O)OC]

diethyl 2-(2-furylmethylene)propanedioate

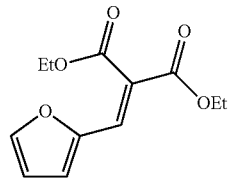 [SMILES: CCOC(=O)C(=Cc1ccco1)C(=O)OCC]

3-[(5-methyl-2-furyl)methylene]pentane-2,4-dione (=STAB 3)

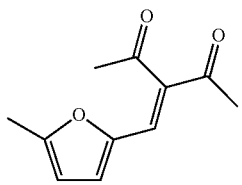

2-[(5-methyl-2-furyl)methylene]propanediol acid

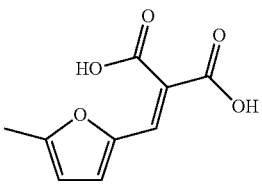

dimethyl 2-[(5-methyl-2-furyl)methylene]propanedioate (=STAB 1)

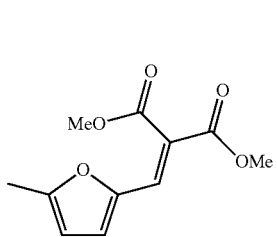 [SMILES: COC(=O)C(=Cc1ccc(C)o1)C(=O)OC]

diethyl 2-[(5-methyl-2-furyl)methylene]propanedioate (=STAB 2)

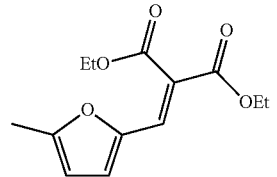 [SMILES: CCOC(=O)C(=Cc1ccc(C)o1)C(=O)OCC]

furan-2-carboxylic acid (=STAB 4)

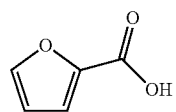

2,5-furandicarboxylic acid

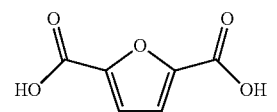

2,3-furandicarboxylic acid

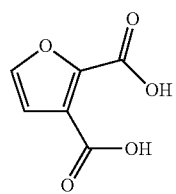 [SMILES: O=C(O)c1ccoc1C(=O)O]

furan-2-carboxylic acid methylester

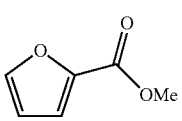

furan-2-carboxylic acid ethylester

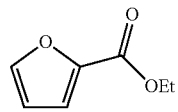

furan-3-carboxylic acid (=STAB 5)

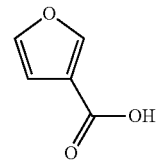

furan-3-carboxylic acid methylester

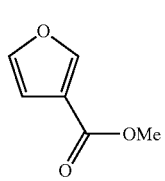

furan-3-carboxylic acid ethylester

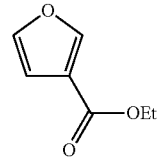

dimethyl-furan-2,5-dicarboxylate

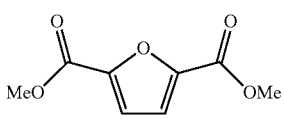 [SMILES: COC(=O)c1ccc(C(=O)OC)o1]

diethyl-furan-2,5-dicarboxylate

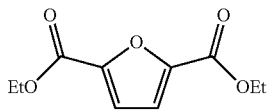 [SMILES: CCOC(=O)c1ccc(C(=O)OCC)o1]

dimethyl-furan-2,3-dicarboxylate

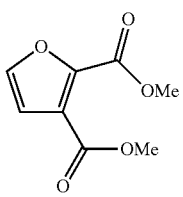 [SMILES: COC(=O)c1ccoc1C(=O)OC]

diethyl-furan-2,3-dicarboxylate

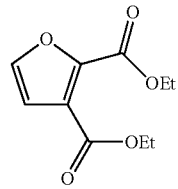 [SMILES: CCOC(=O)c1ccoc1C(=O)OCC]

3,4-furandicarboxylic acid

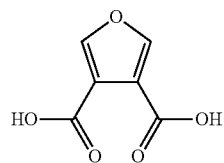 [SMILES: O=C(O)c1cocc1C(=O)O]

dimethyl-furan-3,4-dicarboxylate

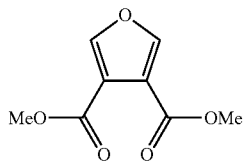 [SMILES: COC(=O)c1cocc1C(=O)OC]

diethyl-furan-3,4-dicarboxylate

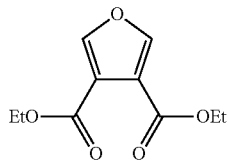 [SMILES: CCOC(=O)c1cocc1C(=O)OCC]

[5-(hydroxymethyl)-2-furyl]methanol (2,5-dihydroxymethylfuran)

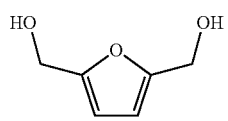

2,5-dichlorofuran

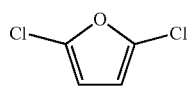

[5-(chloromethyl)-2-furyl]methanol

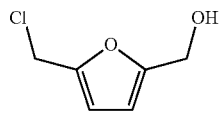

2-benzyl-5-methyl-furan

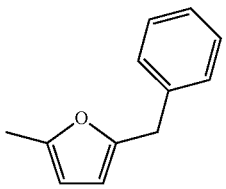

2,5-dibenzylfuran

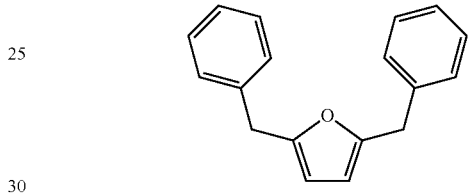

Within the aforementioned group of compounds of the formula (I), the following substances are once again explicitly stated:
3-(2-furylmethylene)pentane-2,4-dione
2-(2-furylmethylene)propanediol acid
dimethyl 2-(2-furylmethylene)propanedioate
diethyl 2-(2-furylmethylene)propanedioate
3-[(5-methyl-2-furyl)methylene]pentane-2,4-dione
2-[(5-methyl-2-furyl)methylene]propanediol acid
dimethyl 2-[(5-methyl-2-furyl)methylene]propanedioate
diethyl 2-[(5-methyl-2-furyl)methylene]propanedioate
furan-2-carboxylic acid
furan-3-carboxylic acid and/or
2,5-furandicarboxylic To achieve optimum fiber protection, the agents as contemplated herein contain compound(s) of the formula (I), preferably in specific quantity ranges. An embodiment is if the agent as contemplated herein contains—relative to the total weight thereof—(a) one or more compounds of the formula (I) in a total quantity of from about 0.1 to about 30.0 wt. %, such as from about 0.2 to about 25.0 wt. %, more preferably from about 0.3 to about 20.0 wt. %.

In a further embodiment, an agent for lightening keratin fibers as contemplated herein contains—relative to the total weight thereof—(a) one or more compounds of the formula (I) in a total quantity of from about 0.1 to about 30.0 wt. %, preferably from about 0.2 to about 25.0 wt. %, more preferably from about 0.3 to about 20.0 wt. %.

(b) Peroxide Compound

The compounds of formula (I) described above are used in the agents as contemplated herein as an active substance for stabilizing, strengthening and invigorating the keratin fibers.

The compounds of the formula (I) ought to be compatible with a plurality of other cosmetic active substances. It emerged that the compounds of the formula (I) show good efficacy in a plurality of different cosmetic hair treatment agents. For example, the compounds of formula (I) are highly compatible both with oxidants, such as those used for oxidative coloring, and also with the reducing agents used to achieve a permanent wave.

Oxidative coloring and permanent waves are hair treatments which usually place the keratin fibers under great stress.

If the an oxidant is added to the agents as contemplated herein, it is possible to prepare a lightning agent that has a strong bleaching effect without the hair becoming fragile, dull or damaged in any other way. Despite the strong lightening effect, the entire hair fiber can be stabilized in this way. The hair protection thus achieved requires little time and can also be applied at the same time as the oxidative coloring step.

In a further most preferred embodiment, an agent as contemplated herein contains (b) at least one peroxide compound from the group of hydrogen peroxide, ammonium peroxodisulfate, potassium peroxodisulfate and/or sodium peroxodisulfate.

In this case, the agent as contemplated herein is an agent for lightening keratin fibers. In other words, an agent for lightening keratin fibers, more particularly human hair, is most preferred as part of this embodiment to contain in a cosmetic carrier:

(a) at least one compound of the formula (I)

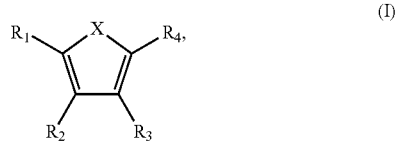

wherein
X denotes oxygen (—O—), sulfur (—S—) or a grouping —$NR_5$—,
$R_1$, $R_2$, $R_3$, $R_4$ denote independently a hydrogen atom, a $C_1$-$C_6$-alkyl group, a $C_2$-$C_6$-alkenyl group, a hydroxy-$C_1$-$C_6$-alkyl group, a $C_2$-$C_6$-alkanoyl group, a carboxyl group, a $C_1$-$C_6$-alkoxy-carbonyl group, a halogen atom, an aryl group, an aryl-$C_1$-$C_6$-alkyl group or the grouping Y,
$R_5$ denotes a $C_1$-$C_6$-alkyl group, a $C_2$-$C_6$-alkenyl group or an aryl group,
Y denotes a grouping of the formula (II),

$R_6$, $R_7$ denote independently a hydrogen atom, a $C_1$-$C_6$-alkyl group, a $C_2$-$C_6$-alkenyl group, a halogen atom, a hydroxy-$C_1$-$C_6$-alkyl group, a $C_2$-$C_6$-alkanoyl group, a carboxyl group, a $C_1$-$C_6$-alkoxy-carbonyl group, a carbamoyl group, a $C_1$-$C_6$-alkylaminocarbonyl group or a di($C_1$-$C_6$)alkylaminocarbonyl group.

(b) contains at least one peroxide compound from the group of hydrogen peroxide, ammonium peroxodisulfate, potassium peroxodisulfate and/or sodium peroxodisulfate.

The expression used in the present disclosure "lightening of keratin fibers" means, more particularly, a bleaching of the fibers. After the lightening agent has been applied, the treated keratin fiber is a lighter shade than before the lightening or bleaching agent is applied. The degree of lightening can, for example, be quantified visually or also by colorimetric measurement of the hair strands (measurement of the lab values). With the colorimetric measurement, the L-value denotes the lightness of a keratin fiber and/or hair strand (when L=100, the hair strand is white diffuse, when L=0, the hair strand is black). After the lightening agent as contemplated herein has been applied, the strand has a correspondingly higher L-value.

As set forth by the present disclosure, the expression used in the present disclosure "lightening of keratin fibers" also means a lightening coloring (or color-bleaching). In this case, the agent can contain, in addition to the peroxide compound, dyes, though such dyes are contained only in small amounts to tint the lightening effect. After the dye-containing lightening agent has been applied, the treated keratin fiber is therefore a lighter shade than before the agent is applied.

The agent as contemplated herein is an agent for lightening (i.e. bleaching and/or color-bleaching) keratin fibers, more particularly human hair. To achieve the lightening effect, the agent therefore contains at least one peroxide compound as the oxidant (b).

Hydrogen peroxide and persulfates (also referred to as peroxide sulfates) are commonly used as suitable peroxide compounds. Ammonium persulfate (ammonium peroxodisulfate), potassium persulfate (potassium peroxodisulfate) and sodium persulfate (sodium peroxodisulfate) are stated as suitable persulfates.

In a further embodiment, an agent for lightening keratin fibers as contemplated herein
(b) contains at least one peroxide compound from the group of hydrogen peroxide, ammonium peroxodisulfate, potassium peroxodisulfate and/or sodium peroxodisulfate.

In a further embodiment, an agent for stabilizing keratin fibers as contemplated herein
(b) contains at least one peroxide compound from the group of hydrogen peroxide, ammonium peroxodisulfate, potassium peroxodisulfate and/or sodium peroxodisulfate.

Hydrogen peroxide is used either in the form of its anhydrous solution and/or in the form of its solid adducts to organic or inorganic compounds, such as urea, melamine and sodium borate. As an embodiment, hydrogen peroxide is used in the form of its anhydrous solution.

The quantity of oxidants in the agent as contemplated herein is from about 0.5 to about 12 wt. %, such as from about 2 to about 10 wt. %, for example from about 3 to about 9 wt. % (calculated as about 100% $H_2O_2$), relative to the total weight of the agent in each case.

Potassium peroxodisulfate is also referred to as potassium persulfate and has the empirical formula $K_2S_2O_8$.

Ammonium peroxodisulfate is also referred to as potassium persulfate and has the empirical formula $(NH_4)_2S_2O_8$.

Sodium peroxodisulfate is also referred to as potassium persulfate and has the empirical formula $Na_2S_2O_8$.

The persulfate(s) may be used in a total quantity of from about 1.0 to about 40.0 wt. %, such as from about 5.0 to about 30.0 wt. %, for example from about 10.0 to about 25 wt. % and in an embodiment from about 15.0 to about 20.0 wt. %, wherein the aforementioned quantity data refer to the total quantity of all persulfates used in the agent, which is made relative to the total weight of the agent.

The bleaching effect can be achieved with the agents which, in addition to hydrogen peroxide, contain at least one persulfate salt. In these agents, the use of the carboxylic acid derivatives of the formula (I) as contemplated herein have proven to be useful.

In a further embodiment, an agent for lightening keratin fibers as contemplated herein contains—relative to the total weight of the agent—

(b1) hydrogen peroxide in a quantity of from about 1.0 to about 10.0 wt. %, such as from about 3.0 to about 8.0 wt. % and (b2) one or more persulfates in a total quantity of from about 10.0 to about 25 wt. %, such as from about 15.0 to about 20.0 wt. %.

In a further embodiment, an agent for stabilizing keratin fibers as contemplated herein contains—relative to the total weight of the agent—

(b1) hydrogen peroxide in a quantity of from about 1.0 to about 10.0 wt. %, such as from about 3.0 to about 8.0 wt. % and (b2) one or more persulfates in a total quantity of from about 10.0 to about 25 wt. %, such as from about 15.0 to about 20.0 wt. %.

In other words, an agent for lightening keratin fibers, more particularly human hair, may contain in a cosmetic carrier—relative to the total weight of the agent in each case—

(a) at least one compound of the formula (I), which is selected from the group of 2-vinylfuran, 2-[(E/Z)-1-propenyl]furan, 2-(2-methyl-1-propenyl)furan, 3-(2-furyl methylene)pentane-2,4-dione, 2-(2-furyl methylene)propanediol acid, dimethyl 2-(2-furyl methylene)propanedioate, diethyl 2-(2-furylmethylene)propandioate, 3-[(5-methyl-2-furyl)methylene]pentane-2,4-dione, 2-[(5-methyl-2-furyl)methylene]propanediol acid, dimethyl 2-[(5-methyl-2-furyl)methylene]propanedioate, diethyl 2-[(5-methyl-2-furyl)methylene]propanedioate, furan-2-carboxylic acid, 2,5-furandicarboxylic acid, 2,3-furandicarboxylic acid, furan-2-carboxylic acid methylester, furan-2-carboxylic acid ethylester, furan-3-carboxylic acid, furan-3-carboxylic acid methylester, furan-3-carboxylic acid ethylester, eimethyl-furan-2,5-dicarboxylate, eiethyl-furan-2,5-dicarboxylate, eimethyl-furan-2,3-dicarboxylate, diethyl-furan-2,3-dicarboxylate, 3,4-furandicarboxylic acid, dimethyl-furan-3,4-dicarboxylate, diethyl-furan-3,4-dicarboxylate, [5-(hydroxymethyl)-2-furyl]methanol (2,5-dihydroxymethylfuran), 2,5-dichlorofuran, [5-(chloromethyl)-2-furyl]methanol, 2-benzyl-5-methyl-furan and/or 2,5-dibenzylfuran and (b1) hydrogen peroxide in a quantity of from about 1.0 to about 10.0 wt. % and (b2) one or more persulfates in a total quantity of from about 10.0 to about 25 wt. %.

In other words, an agent for lightening keratin fibers, more particularly human hair, may contain in a cosmetic carrier—relative to the total weight of the agent in each case—

(a) at least one compound of the formula (I), which is selected from the group of 2-vinylfuran, 2-[(E/Z)-1-propenyl]furan, 2-(2-methyl-1-propenyl)furan, 3-(2-furylmethylene)pentane-2,4-dione, 2-(2-furylmethylene)propane diol acid, dimethyl 2-(2-furyl methylene)propanedioate, diethyl 2-(2-furyl methylene)propandioate, 3-[(5-methyl-2-furyl)methylene]pentane-2,4-dione, 2-[(5-methyl-2-furyl)methylene]propanediol acid, dimethyl 2-[(5-methyl-2-furyl)methylene]propanedioate, diethyl 2-[(5-methyl-2-furyl)methylene]propanedioate, furan-2-carboxylic acid, 2,5-furandicarboxylic acid, 2,3-furandicarboxylic acid, furan-2-carboxylic acid methylester, furan-2-carboxylic acid ethylester, furan-3-carboxylic acid, furan-3-carboxylic acid methylester, furan-3-carboxylic acid ethylester, eimethyl-furan-2,5-dicarboxylate, eiethyl-furan-2,5-dicarboxylate, eimethyl-furan-2,3-dicarboxylate, diethyl-furan-2,3-dicarboxylate, 3,4-furandicarboxylic acid, dimethyl-furan-3,4-dicarboxylate, diethyl-furan-3,4-dicarboxylate, [5-(hydroxymethyl)-2-furyl]methanol (2,5-dihydroxymethylfuran), 2,5-dichlorofuran, [5-(chloromethyl)-2-furyl]methanol, 2-benzyl-5-methyl-furan and/or 2,5-dibenzylfuran and (b1) hydrogen peroxide in a quantity of from about 3.0 to about 8.0 wt. % and (b2) one or more persulfates in a total quantity of from about 15.0 to about 20.0 wt. %.

pH Value

The agents for stabilizing keratin fibers as contemplated herein may be from a hydrous cosmetic carrier. The pH value of this agent can be set from about 2 to about 12.

If the agent as contemplated herein is to be packaged in the form of a shampoo or a conditioner, the pH value is most preferably set to a range of from about 2.5 to about 6.5.

If, on the other hand, the agent as contemplated herein is to be packaged in the form of a lightening agent, the pH value may be set to a value of from about 7.5 to about 12.5. During the work that led to this present disclosure, it emerged that the pH value for achieving a useful lightening effect is a result-effective variable.

It was observed, for example, that a bleaching effect is achieved by treating the hair with an agent set to a pH value above about 8.0, such as above about 8.5, and for example above about 9.0. However, setting pH values above about 11.0, in some embodiments, may be avoided in order to prevent excessive hair damage and also increased skin irritation.

In a further embodiment, an agent for lightening keratin fibers as contemplated herein (c) contains water and has a pH value in the range of from about 7.5 to about 12.5.

In a further embodiment, an agent for lightening keratin fibers as contemplated herein (c) contains water and has a pH value in the range of from about 8.0 to about 10.5, such as from about 8.5 to about 10.0 and for example from about 9.0 to about 10.0.

In other words, an agent for lightening keratin fibers, more particularly human hair, may contain in a cosmetic carrier—relative to the total weight of the agent in each case—

(a) at least one compound of the formula (I), which is selected from the group of 2-vinylfuran, 2-[(E/Z)-1-propenyl]furan, 2-(2-methyl-1-propenyl)furan, 3-(2-furylmethylene)pentane-2,4-dione, 2-(2-furylmethylene)propane diol acid, dimethyl 2-(2-furylmethylene)propanedioate, diethyl 2-(2-furylmethylene)propandioate, 3-[(5-methyl-2-furyl)methylene]pentane-2,4-dione, 2-[(5-methyl-2-furyl)methylene]propanediol acid, dimethyl 2-[(5-methyl-2-furyl)methylene]propanedioate, diethyl 2-[(5-methyl-2-furyl)methylene]propanedioate, furan-2-carboxylic acid, 2,5-furandicarboxylic acid, 2,3-furandicarboxylic acid, furan-2-carboxylic acid methylester, furan-2-carboxylic acid ethylester, furan-3-carboxylic acid, furan-3-carboxylic acid methylester, furan-3-carboxylic acid ethylester, eimethyl-furan-2,5-dicarboxylate, eiethyl-furan-2,5-dicarboxylate, eimethyl-furan-2,3-dicarboxylate, diethyl-furan-2,3-dicarboxylate, 3,4-furandicarboxylic acid, dimethyl-furan-3,4-dicarboxylate, diethyl-furan-3,4-dicarboxylate, [5-(hydroxymethyl)-2-furyl]methanol (2,5-dihydroxymethylfuran), 2,5-dichlorofuran, [5-(chloromethyl)-2-furyl]methanol, 2-benzyl-5-methyl-furan and/or 2,5-dibenzylfuran and (b1) hydrogen peroxide in a quantity of from about 1.0 to about 10.0 wt. % and (b2) one or more persulfates in a total quantity of from about 10.0 to about 25 wt. % and (c) water, wherein the agent has a pH value in the range of from about 8.5 to about 10.0.

In other words, an agent for lightening keratin fibers, more particularly human hair, may contain in a cosmetic carrier—relative to the total weight of the agent in each case—(a) at least one compound of the formula (I), which is selected from the group of 2-vinylfuran, 2-[(E/Z)-1-propenyl]furan, 2-(2-methyl-1-propenyl)furan, 3-(2-furylmethylene)pentane-2,4-dione, 2-(2-furylmethylene)propanediol acid, dimethyl 2-(2-furylmethylene)propanedioate, diethyl 2-(2-furylmethylene)propandioate, 3-[(5-methyl-2-furyl)methylene]pentane-2,4-dione, 2-[(5-methyl-2-furyl)methylene]propanediol acid, dimethyl 2-[(5-methyl-2-furyl)methylene]propanedioate, diethyl 2-[(5-methyl-2-furyl)methylene]propanedioate, furan-2-carboxylic acid, 2,5-furandicarboxylic acid, 2,3-furandicarboxylic acid, furan-2-carboxylic acid methylester, furan-2-carboxylic acid ethylester, furan-3-carboxylic acid, furan-3-carboxylic acid methylester, furan-3-carboxylic acid ethylester, eimethyl-furan-2,5-dicarboxylate, eiethyl-furan-2,5-dicarboxylate, eimethyl-furan-2,3-dicarboxylate, diethyl-furan-2,3-dicarboxylate, 3,4-furandicarboxylic acid, dimethyl-furan-3,4-dicarboxylate, diethyl-furan-3,4-dicarboxylate, [5-(hydroxymethyl)-2-furyl]methanol (2,5-dihydroxymethyl-furan), 2,5-dichlorofuran, [5-(chloromethyl)-2-furyl]methanol, 2-benzyl-5-methyl-furan and/or 2,5-dibenzylfuran and (b1) hydrogen peroxide in a quantity of from about 3.0 to about 8.0 wt. % and (b2) one or more persulfates in a total quantity of from about 15.0 to about 20.0 wt. %, and (c) water, wherein the agent has a pH value in the range of from about 9.0 to about 10.0.

The pH value can be measured by employing a gas electrode, for example, which is commercially available in the form of a combination electrode. Before the pH value is measured, the gas electrodes are calibrated with calibration solutions of a known pH value. The pH values as defined by the present disclosure are pH values that were measured at a temperature of 22° C.

The suitable pH value can be set by employing various alkalizing agents. Suitable alkalizing agents as contemplated herein are selected from ammonia, alkanolamines, alkali metal hydroxides, alkali metal metasilicates, alkali metal phosphates and alkali metal hydrogen phosphates. Suitable inorganic alkalizing agents are sodium hydroxide, sodium hydroxide, sodium silicate and sodium metasilicate. Organic alkalizing agents usable as contemplated herein are selected from monoethanolamine, 2-amino-2-methylpropanol and triethanolamine. Sodium silicate and sodium metasilicate are employed in embodiments.

In a further embodiment, an agent for lightening keratin fibers as contemplated herein contains sodium silicate and/or sodium metasilicate as the alkalizing agent.

Sodium silicates are the sodium salts of various silica. A distinction can be drawn between sodium silicates with a ratio of silicon dioxide to sodium monoxide that is equal to about 2 or smaller than about 1. The latter group includes sodium metasilicate, i.e. sodium metasilicates are polymer silicates of the formula $[Na_2SiO_3]_x$. Sodium metasilicate can be used in its anhydrous form or in the form of its hydrates.

Moreover, sodium silicate can also be used in the form of sodium water glass. Sodium water glass is an amorphous sodium silicate solidified from a melt.

For example, sodium water glass (also referred to as natron water glass) is commercially available from BASF and bears the CAS number 1344-09-8. The raw material is sold in the form of an anhydrous solution with a $SiO_2$ content of approx. 29 wt. % and a $Na_2O$ content of approx. 9 wt. %.

To set an acid pH value, the acidification agents normally employed in the cosmetic sector can be used. Acidification agents suitable as contemplated herein include citric acid, lactic acid, acetic acid and diluted mineral acids (such as hydrochloric acid, sulfuric acid, phosphoric acid).

Kit-of-Parts

To carry out the bleaching and/or lightening process described above, the use finds it convenient if all the components required to do so are provided in the form of a kit-of-parts.

A second subject matter of the present disclosure, therefore, is a kit-of-parts for lightening keratin fibers, packed separately from one another, and including:

a container (i) containing an anhydrous cosmetic agent (A) and a container (ii) containing an anhydrous cosmetic agent (B), wherein agent (A) contains hydrogen peroxide and agent (B) contains at least one persulfate and at least one compound of the formula (I), wherein the compound of the formula (I) has been disclosed in detail in the description of the first subject matter of the present disclosure, and wherein the mixture of agents (A) and (B) has a pH value in the range of from about 7.5 to about 12.5.

In other words, the second subject matter of the present disclosure may include: a kit-of-parts for lightening keratin fibers, packed separately from one another, and including:

a container (i) containing an anhydrous cosmetic agent (A) and a container (ii) containing an anhydrous cosmetic agent (B), wherein agent (A) contains hydrogen peroxide and agent (B) contains at least one persulfate and at least one compound of the formula (I),

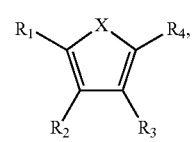

(I)

wherein

X denotes oxygen (—O—), sulfur (—S—) or a grouping —NR$_5$—, $R_1$, $R_2$, $R_3$, $R_4$ denote independently a hydrogen atom, a $C_1$-$C_6$-alkyl group, a $C_2$-$C_6$-alkenyl group, a hydroxy-$C_1$-$C_6$-alkyl group, a $C_2$-$C_6$-alkanoyl group, a carboxyl group, a $C_1$-$C_6$-alkoxy-carbonyl group, a halogen atom, an aryl group, an aryl-$C_1$-$C_6$-alkyl group or the grouping Y, $R_5$ denotes a $C_1$-$C_6$-alkyl group, a $C_2$-$C_6$-alkenyl group or an aryl group, Y denotes a grouping of the formula (II),

$R_6$, $R_7$ denote independently a hydrogen atom, a $C_1$-$C_6$-alkyl group, a $C_2$-$C_6$-alkenyl group, a halogen atom, a hydroxy-$C_1$-$C_6$-alkyl group, a $C_2$-$C_6$-alkanoyl group, a carboxyl group, $C_1$-$C_6$-alkoxy-carbonyl group, a carbamoyl group, a $C_1$-$C_6$-alkylaminocarbonyl group or a di($C_1$-$C_6$)alkylaminocarbonyl group,
wherein the mixture of agents (A) and (B) has a pH value in the range of from about 7.5 to about 12.5.

Agent (A) contains water and hydrogen peroxide. In an embodiment, the water content of agent (A)—relative to the total weight of agent (A)—is from about 50 to about 90 wt. %

As contemplated herein, agent (B) is anhydrous. As used in the present disclosure, anhydrous means that the water content in agent (B)—relative to the total weight of agent (B)—is a maximum of 5.0 wt. %, preferably 1.0 wt. %, for example a maximum of 0.1 wt. %.

The anhydrous agent (B) contains, in addition to at least one persulfate (which can alternatively be referred to as peroxodisulfate), at least one carboxylic acid ester of the formula (I).

To produce the ready-for-use agent, agents (A) and (B) are mixed together. The mixing ratio in which agents (A) and (B) are mixed together is preferably from about 1:5 to about 5:1, preferably from about 1:3 to about 3:1, more preferably from about 2:1 to about 1:2.

For example:
about 100 g of agent (A) are mixed with about 50 g of agent (B),
about 100 g of agent (A) are mixed with about 100 g of agent (B), or
about 50 g of agent (A) are mixed with about 100 g of agent (B).

The pH value of the mixture from agents (A) and (B) is in the range of from about 7.5 to about 12.5, such as in the range of from about 8.0 to about 10.5, for example from about 8.5 to about 10.0 and in an embodiment from about 9.0 to about 10.0.

Moreover, it has emerged that providing anhydrous agent (B) in the form of a paste or cream is suitable. For this purpose, agent (B) contains—relative to the total weight of agent (B)—one or more fatty constituents in a total quantity of at least 20 wt. %. The most preferable embodiment is for agent (B)—relative to the total weight of agent (B)—to contain one or more fatty constituents in a total quantity of at least 30 wt. %.

As used in the present disclosure, "fatty constituents" are organic compounds with a water solubility at room temperature (22° C.) and atmospheric pressure (760 mmHg) of less than 1 wt. %, such as less than 0.1 wt.-%. The definition of fatty constituents explicitly includes only uncharged (i.e. non-ionic) compounds. Fatty constituents have at least one saturated or unsaturated alkyl group with at least 8 C-atoms. The molecular weight of the fatty constituents is a maximum of about 5000 g/mol, such as a maximum of about 2500 g/mol and in an embodiment a maximum of about 1000 g/mol. The fatty constituents are neither polyoxyalkylated nor polyglycerylated compounds.

Exemplary fatty constituents in this context are the constituents from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons. The present disclosure explicitly considers only non-ionic substances to be fatty constituents. Charged compounds such as fatty acids and their salts are not considered to be fatty constituents, in some embodiments.

The $C_{12}$-$C_{30}$ fatty alcohols can be saturated, mono or poly-unsaturated, linear or branched fatty alcohols with from about 12 to about 30 C-atoms.

Examples of linear, saturated $C_{12}$-$C_{30}$ fatty alcohols are dodecan-1-ol (dodecylalcohol, laurylalcohol), tetradecan-1-ol (tetradecyl alcohol, myristyl alcohol), hexadecan-1-ol (hexadecyl alcohol, cetyl alcohol, palmityl alcohol), octadecan-1-ol (octadecyl alcohol, stearyl alcohol), arachyl alcohol (eicosan-1-ol), heneicosyl alcohol (heneicosan-1-ol) and/or behenyl alcohol (docosan-1-ol).

Exemplary linear, unsaturated fatty alcohols are (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenoyl alcohol), gadoleyl alcohol ((9Z)-eicos-9-en-1-ol), arachidon alcohol ((5Z,8Z,11Z,14Z)-eicosa-5,8,11,14-tetraen-1-ol), erucyl alcohol ((13Z)-docos-13-en-1-ol) and/or brassidyl alcohol ((13E)-docosen-1-ol).

Exemplary branched fatty alcohols are 2-octyl-dodecanol, 2-hexyl-dodecanol and/or 2-butyl-dodecanol.

As used in the present disclosure, a $C_{12}$-$C_{30}$ fatty acid triglyceride is the triester of the trivalent alcohol glycerine with three equivalent fatty acids. Both identically structured and different fatty acids within a triglyceride molecule can be involved in the ester formation.

As used in the present disclosure, fatty acids are saturated or unsaturated, unbranched or branched, unsubstituted or substituted $C_{12}$-$C_{30}$ carboxylic acids. Unsaturated fatty acids can be monounsaturated or polyunsaturated. The C—C double bond(s) of an unsaturated fatty acid can have the cis- or trans configuration.

Fatty acid triglycerides are exemplified by their suitability, for which at least one of the ester groups, based on glycerine, is formed with a fatty acid, which is selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enic acid], oleic acid [(9Z)-octadec-9-enic acid], elaidinic acid [(9E)-octadec-9-enic acid], eruca acid [(13Z)-docos-13-enic acid], linoleic acid [(9Z,12Z)-octadeca-9,12-dienic acid, linoleic acid [(9Z,12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-trienoic acid] and/or nervonic acid [(15Z)-tetracos-15-enic acid].

The fatty acid triglycerides can also be from natural sources. The fatty acid triglycerides occurring in soy bean oil, peanut oil, sunflower oil, macadamia nut oil, drumstick tree oil, apricot kernel oil, manila oil and/or possibly hardened caster oil, and the mixtures thereof are suitable for use in the product as contemplated herein.

A $C_{12}$-$C_{30}$ fatty acid monoglyceride is the monoester of the trivalent alcohol glycerin with an equivalent fatty acid. Either the middle hydroxy group of the glycerine or the final hydroxy group of the glycerin can be esterified with the fatty acid.

The $C_{12}$-$C_{30}$ fatty acid triglycerides are exemplified by their suitability, for which at least one hydroxy group of the glycerine is esterified, wherein the fatty acids are selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enic acid], oleic acid [(9Z)-octadec-9-enic acid], elaidinic acid [(9E)-octadec-9-enic acid], eruca acid [(13Z)-docos-13-enic acid], linoleic acid [(9Z,12Z)-octadeca-9,12-dienic acid, linoleic acid [(9Z,12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-trienoic acid] and/or nervonic acid [(15Z)-tetracos-15-enic acid].

A $C_{12}$-$C_{30}$ fatty acid diglyceride is the diester of the trivalent alcohol glycerine with two equivalent fatty acids. Either the middle and a terminal hydroxy group of the glycerine can be esterified with two equivalents of fatty acid or both terminal hydroxy groups of the glycerin are each esterified with one fatty acid. The glycerin can be esterified with two identically structured or two different fatty acids.

Fatty acid diglycerides are exemplified by their suitability, for which at least one of the ester groups, based on glycerin, is formed with a fatty acid, which is selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enic acid], oleic acid [(9Z)-octadec-9-enic acid], elaidinic acid [(9E)-octadec-9-enic acid], eruca acid [(13Z)-docos-13-enic acid], linoleic acid [(9Z,12Z)-octadeca-9,12-dienic acid, linoleic acid [(9Z,12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-trienoic acid] and/or nervonic acid [(15Z)-tetracos-15-enic acid].

Hydrocarbons are exclusively compounds including only the atoms carbon and hydrogen with 8 to 80 C-atoms. In this context, aliphatic hydrocarbons such as mineral oils, liquid paraffin oils (e.g. paraffinum liquidum or paraffinum perliquidum), isoparaffin oils, semi-solid paraffin oils, paraffin waxes, hard paraffin (paraffinum solidum), vaseline and polydecene are exemplary.

In this context, liquid paraffin oils (paraffinum liquidum and paraffinum perliquidum) have proven to be suitable. A suitable hydrocarbon is paraffinum liquidum, also referred to as white oil. Paraffinum liquidum is a mixture of cleaned, saturated, aliphatic hydrocarbons, which mainly includes hydrogen chains with a C-chain distribution from 25 to 35 C-atoms.

In another embodiment, a kit-of-parts is accordingly exemplified in that agent (B)—relative to the total weight of agent (B)—contains one or more fatty constituents in a total quantity of at least 20 wt. %, wherein the fatty constituents are selected from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons.

In another embodiment, a kit-of-parts is accordingly exemplified in that agent (B)—relative to the total weight of agent (B)—contains one or more fatty constituents in a total quantity of at least 30 wt. %, wherein the fatty constituents are selected from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons.

With respect to the embodiments of the kit-of-parts as contemplated herein, the agents mentioned in the present disclosure apply mutatis mutandis.

Other Constituents

The agents as contemplated herein (and/or agents (A) and (B) of the kit-of-parts) can also contain other active substances, excipients and additional components, such as cationic surfactants, non-ionic surfactants, amphoteric and/or zwitterionic surfactants, anionic surfactants, anionic, non-ionic and/or cationic polymers, structurants such as glucose, perfume oils, fiber structure-improving active substances, such as mono-, di- and oligosaccharides such as glucose, galactose, fructose, laevulose and lactose; dyes for coloring the agent: anti-dandruff substances such as piroctone olamine, zinc omadine and climbazole; amino acids and oligopeptides; animal and/or plant-based hydrolyzed proteins, and also in the form of their fatty acid condensation products or possible anionically or cationically modified derivatives; vegetable oils; light stabilizers and UV blockers; active ingredients such as panthenol, pantothenic acid, pantolacton, allantoin, pyrrolidinon carboxylic acid and their color-changing salts, as well bisabolol; polyphenols, more particularly hydroxycinnamic acids, 6,7-dihydroxycumarine, hydroxybenzoic acids, catechines, tannins, leucoanthocyanidins, anthocyanidins, flavanons, flavons and flavonols; vitamins, provitamins and vitamin precursors; plant extracts; source and penetration substances such as glycerin, propylene glycol monoethyl ether, carbonates, hydrogen carbonates, guanidines, ureas, as well as primary, secondary and tertiary phosphates; pacifiers such as latex, styrene/PVP- and styrene/acrylamide copolymers; pearl-shine agents such as ethylene glycol mono- and -distearate as well as PEG-3-distearate; pigments and propellants such as propane-butane mixtures, $N_2O$, dimethyl ether, $CO_2$ and air.

In the agents as contemplated herein, each of the additional active substances and excipients are used in quantities of from about 0.0001 to about 10 wt. %, such as from about 0.0005 to about 5 wt. %, relative to the total weight of agent (A) and/or the peroxide compound preparation (B).

Dyes

Insofar as the agent as contemplated herein is an agent for coloring bleaching (i.e. for tinting the bleaching effect), the agent can also contain small quantities of at least one oxidizing dye precursor and/or at least one partially-oxidizing dye.

Oxidative dyes are produced with oxidizing dye precursors on the basis of developer and coupler components on the keratin fiber. Oxidizing dye precursors of the developer type include
p-phenylendiamine, p-toluylendiamine, N,N-bis-(β-hydroxyethyl)-p-phenylendiamine, 4-N,N-bis-(β-hydroxyethyl)-amino-2-methylaniline, 2-(β-hydroxyethyl)-p-phenylendiamine, 2-(α,β-dihydroxyethyl)-p-phenylendiamine, 2-hydroxymethyl-p-phenylendiamine, bis-(2-hydroxy-5-aminophenyl)-methane, p-aminophenol, 4-amino-3-methylphenol, 2,4,5,6-tetraaminopyrimidine, 4-hydroxy-2,5,6-triaminopyrimidine, 2-hydroxy-4,5,6-triaminopyrimidine and/or 4,5-diamino-1-(β-hydroxyethyl)-pyrazol.

Oxidizing dye precursors of the coupler type include m-phenylenediamine derivatives, naphthols, resorcinol and resorcinol derivatives, pyrazolones and m-aminophenol derivatives. Particularly suitable coupler substances are 1-naphthol, 1,5-, 2,7- and 1,7-dihydroxy naphthaline, 5-amino-2-methylphenol, m-aminophenol, resorcinol, resorcinol monomethyl ether, m-phenylenediamine, 1-phenyl-3-methyl-pyrazolone-5,2,4-dichloro-3-aminophenol, 1,3-bis-(2',4'-diaminophenoxy)-propane, 2-chloro-resorcinol, 4-chloro-resorcinol, 2-chloro-6-methyl-3-aminophenol, 2-amino-3-hydroxypyridine, 2-methylresorcinol, 5-methylresorcinol and 2-methyl-4-chloro-5-aminophenol, 1-naphthol, 1,5-dihydroxynaphthaline, 2,7-dihydroxynaphthaline, 1,7-dihydroxynaphthaline, 3-aminophenol, 5-amino-2-methylphenol, 2-amino-3-hydroxypyridine, resorcinol, 4-chlororesorcinol, 2-chloro-6-methyl-3-aminophenol, 2-methylresorcinol, 5-methylresorcinol, 2,5-dimethylresorcinol and 2,6-dihydroxy-3,4-dimethylpyridine.

The dyes used in step (I) of the method can also contain one or more partially-oxidizing dyes. Nitrophenylendiamines, nitroaminophenols, azo dyes, anthrachinones or indophenoles are suitable partially-oxidizing dyes. Exemplary partially-oxidizing dyes are the compounds known under the international designations and/or trade names HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 12, Disperse Blue 3, Acid Blue 7, Acid Green 50, HC Violet 1, Disperse Violet 1, Disperse Violet 4, Acid Violet 43, Disperse Black 9, Acid Black 1, and Acid Black 52, as well as 1,4-diamino-2-nitrobenzol, 2-amino-4-nitrophenol, 1,4-bis-(β-hydroxyethyl)-amino-2-nitrobenzol, 3-nitro-4-(β-hydroxyethyl)-aminophenol, 2-(2'-hydroxyethyl)amino-4,6-dinitrophenol, 1-(2'-hydroxyethyl)amino-4-methyl-2-nitrobenzol, 1-amino-4-(2'-hydroxyethyl)-amino-5-chloro-2-nitrobenzol, 4-amino-3-nitrophenol, 1-(2'-ureidoethyl)amino-4-nitrobenzol, 4-amino-2-nitrodiphenylamine-2'-carboxylic acid, 6-nitro-1,2,3,4-tetrahydrochinoxaline, 2-hydroxy-1,4-naphthochinon, picric acid and the salts thereof, 2-amino-6-chloro-4-nitrophenol, 4-ethylamino-3-nitrobenzoic acid and 2-chloro-6-ethylamino-1-hydroxy-4-nitrobenzol.

Moreover, the substrates to be de-colorized can also be dyed with natural, partially-oxidizing dyes that occur in nature, such as Henna red, Henna neutral, Henna black, chamomile blossoms sandalwood, black tea, Cascara bark, sage, logwood, madder root, catechu, cedar and alkanna root.

The aforementioned dyes are used in a total quantity of below about 1.0 wt. %, such as in a total quantity of below about 0.5 wt. %, for example in a total quantity of below about 0.1 wt. %—relative to the total weight of each agent as contemplated herein.

EXAMPLES

1. Formulations

The following formulations were created (all data in wt. %)

1.1. Formulation with Hydrogen Peroxide (Agent (A))

| Substance (INCI) | OX |
|---|---|
| Sodium benzoate | 0.04 |
| Dipicolinic acid | 0.10 |
| Disodium pyrophosphate | 0.10 |
| Potassium hydroxide 50% | 0.19 |
| Propanediol-1,2 | 0.50 |
| HEDP 60% | 0.25 |
| Paraffinum Liquidum | 2.00 |
| Cetearyl Alcohol | 3.60 |
| Ceteareth-20 | 1.20 |
| Hydrogen peroxide 50% | 12.20 |
| Water, demineralized | ad 100 |

1.2. Paste with Compounds of the Formula (I) and Persulfate (Agent (B))

| Substance (INCI) | V1 | E1 | E2 | E3 | E4 | E5 |
|---|---|---|---|---|---|---|
| Versagel M1600 | 5.00 | 5.00 | 5.00 | 5.00 | 5.00 | 5.00 |
| Lanette N | 7.00 | 7.00 | 7.00 | 7.00 | 7.00 | 7.00 |
| Eumulgin B 5 | 4.00 | 4.00 | 4.00 | 4.00 | 4.00 | 4.00 |
| Xanthan NaTrue | 1.50 | 1.50 | 1.50 | 1.50 | 1.50 | 1.50 |
| Sodium metasilicate (anhydrous) | 6.50 | 6.50 | 6.50 | 6.50 | 6.50 | 6.50 |
| Potassium persulfate | 42.00 | 42.00 | 42.00 | 42.00 | 42.00 | 42.00 |
| L-Serin | 0.20 | 0.20 | 0.20 | 0.20 | 0.20 | 0.20 |
| Perfume | 0.60 | 0.60 | 0.60 | 0.60 | 0.60 | 0.60 |
| Dimethyl 2-[(5-methyl-2-furyl)methylene]propanedioate (STAB 1) | — | 18.4 | — | — | — | — |
| Diethyl 2-[(5-methyl-2-furyl)methylene]propanedioate (STAB 2) | — | — | 20.2 | — | — | — |
| 3-[(5-Methyl-2-furyl)methylen]pentan-2,4-dion (STAB 3) | — | — | — | 16.2 | — | — |
| Furan-2-carboxylic acid (=STAB 4) | — | — | — | — | 10.2 | — |
| Furan-3-carboxylic acid (=STAB 5) | — | — | — | — | — | 10.2 |
| Paraffinum Liquidum | ad 100 | ad 100 | ad 100 | ad 100 | ad 100 | ad 100 |

Versagel M1600: Paraffinum liquidum (mineral oil), ethylene/propylene/styrene copolymer, butylene/ethylene/styrene copolymer Lanette N: Cetearyl alcohol, sodium cetearyl sulfate Eumulgin B 5: Ceteareth-50

Xanthan NaTrue: Xanthan Gum

Dimethyl 2-[(5-methyl-2-furyl)methylene]propanedioate (STAB 1)

Diethyl 2-[(5-methyl-2-furyl)methylene]propanedioate (STAB 2)

3-[(5-Methyl-2-furyl)methylene]pentane-2,4-dione (STAB 3)

Obtained by the known method based on methylfurfural (Memarian, H. R.; Abdoli-Senejani, M.; Doepp, D., Magazine for natural research B, 2006, 61(1), 50-56)/carbolxylic acid ester (Kazancioglu, E. A.; Kazancioglu, M. Z.; Fistikci, M., Secen, H.; Altundas, R., Organic Letters, 2013, 5 (18), 4790-4793).

Furan-2-carbolxylic acid (STAB 4) was purchased
Furan-3-carbolxylic acid (STAB 5) was purchased.

The hydrocarbon peroxide formulation (OX) and the persulfate paste (V1, as well as E1, E2, E3 and E4) were mixed in the ratio of 1:1 and applied to 2 strands of hair immediately after mixing (treatment time 30 min at room temperature). The pH value of the application mixture was 9.5. After the treatment time, the strands were rinsed, dried and, after 48 hours, measured by employing Difference Scanning calorimetry (2 samples per strand).

2. Fiber Stability Measurement

The following fusion points were determined by employing a DSC analysis (Perkin Elmer DSC-7).
A precise description of the method can be found in DE 196 173 95 A1, for example.
The higher the measured value, the more stable the keratin matrix of the hair.

Hair Stability

|  | Reference, untreated strands | OX + V1 | OX + E1 | OX + E2 | OX + E3 | OX + E4 | OX + E5 |
| --- | --- | --- | --- | --- | --- | --- | --- |
| DSC: Peak Apex Temp. (° C.) | 152 | 139 | 146 | 141 | 149 | 163 | 152 |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An agent for stabilizing keratin fibers comprising a cosmetic carrier and:
    (a) furan-2-carboxylic acid in a total quantity of from about 0.3 to 20.0 wt. %; and
    (b1) hydrogen peroxide in a quantity of from about 1.0 to about 10.0 wt. %, and
    (b2) one or more persulfates in a total quantity of from about 10.0 to about 25 wt. %,
    wherein all amounts are based on the total weight of the agent.

2. The agent according to claim 1, wherein the agent further comprises:
    (c) water,
    and wherein the agent has a pH value in a range of from about 7.5 to about 12.5.

3. The agent according to claim 1, wherein the keratin fibers comprise human hair.

4. The agent according to claim 1, wherein the agent comprises, relative to the total weight of the agent:
    (b1) hydrogen peroxide in a quantity of from about 3.0 to about 8.0 wt. %, and
    (b2) one or more persulfates in a total quantity of from about 15.0 to about 20.0 wt. %.

5. A kit-of-parts for lightening keratin fibers, packed separately from one another and comprising:
    a container (i) containing a cosmetic agent (A), wherein agent (A) comprises water and hydrogen peroxide with water present in an amount of from about 50 to about 90 wt. % based on the total weight of agent (A); and
    a container (ii) containing an anhydrous cosmetic agent (B), wherein agent (B) comprises at least one persulfate and furan-2-carboxylic acid;
    wherein agent (B)—relative to the total weight of agent (B)—further comprises one or more fatty constituents in a total quantity of at least 20 wt. %;
    wherein the mixture of agents (A) and (B) has a pH value in the range of from about 7.5 to about 12.5; and
    wherein the mixture of agents (A) and (B) comprises the furan-2-carboxylic acid in a total quantity of from about 0.3 to 20.0 wt. %, the hydrogen peroxide in a total quantity of from about 1.0 to about 10.0 wt. %, and the at least one persulfate in a total quantity of from about 10.0 to about 25 wt. %, wherein all amounts are based on the total weight of the mixture.

* * * * *